United States Patent [19]

Smith et al.

[11] Patent Number: 5,412,995
[45] Date of Patent: May 9, 1995

[54] SINGLE-PLY ROOF COVER FATIGUE TESTER

[75] Inventors: Phillip J. Smith, Belmont; George A. Smith, Littleton, both of Mass.

[73] Assignee: Factory Mutual Research Corporation, Norwood, Mass.

[21] Appl. No.: 258,061

[22] Filed: Jun. 10, 1994

[51] Int. Cl.$^6$ .............................................. G01N 3/08
[52] U.S. Cl. ........................................ 73/808; 73/159; 73/865.6
[58] Field of Search ................... 73/159, 808, 810–812, 73/816, 817, 865.6

[56] References Cited

U.S. PATENT DOCUMENTS

| | | |
|---|---|---|
| 2,849,877 | 9/1958 | Burgett et al. |
| 3,460,379 | 8/1969 | Webb ............................... 73/159 |
| 3,942,362 | 3/1976 | Keller .............................. 73/816 |
| 4,869,111 | 9/1989 | Ohya et al. |

Primary Examiner—Robert Raevis
Attorney, Agent, or Firm—Lane, Aitken & McCann

[57] ABSTRACT

A single-ply roof cover fatigue tester includes an adjustable platen to which a roof cover sample is attached. Movement of the platen relative to a support frame adjusts the angle at which a tension force is applied to the sample by fluid pressure cylinders. The platen is long enough to accommodate the roof cover sample and three associated fasteners in a straight line at a spacing commonly used in actual roof cover installations. A control system controls the flow of pressure fluid to fluid pressure cylinders on opposite sides of the sample to alternately increase the tension on one side and then the other, while maintaining a minimum tension on the opposite side. A counter is provided to indicate the number of times the increasing tension alternates from one side to the other.

14 Claims, 5 Drawing Sheets

SINGLE-PLY ROOF COVER FATIGUE TESTER

BACKGROUND OF THE INVENTION

The present invention relates to a method and apparatus for evaluating the wind-induced fatigue performance of mechanically attached single-ply membrane roof covers.

Known ultimate load, static test methods and apparatus do not address the cyclic nature of wind loads. Although these tests are adequate in preventing non-fatigue failures of properly installed roof systems, they cannot determine the likelihood of the failure of a roof membrane due to fatigue. Mechanical securement of single-ply membranes is fast becoming one of the more popular installation methods due to its lower installation cost. In this installation method, insulation is secured to a structural roof deck with a minimum number of fasteners, usually one fastener for every four to eight square feet of insulation. A single-ply roof membrane is rolled out over the insulation and attached, through the insulation, to the roof deck at discrete points using mechanical fasteners. Wind-induced uplift pressure is transferred directly from the membrane through the fasteners to the structural deck. Field experience with this roofing system has revealed that fatigue failure modes of fastener twist-out, steel deck fatigue and membrane fatigue do not occur in the known static wind uplift tests.

Other apparatuses are known which evaluate the fatigue of fasteners. In one apparatus, a motordriven cam oscillates a lever which is connected, through an air cylinder and chain, to a membrane secured by a fastener. A test on the apparatus is typically run with the same load applied to a membrane sample, at the same angle, regardless of the material of the membrane. Under actual conditions, a given wind applies loads to different roof cover materials at different angles. The common load and angle applied by the known apparatus for all materials results in the simulation of different wind loads for different materials. Furthermore, with respect to the apparatus itself, it loads one side of the fastener while maintaining a zero load on the other side. This approach is overly severe in that it simulates the membrane on one side of a row of fasteners being inflated by the wind while the other side of the fasteners has no load applied. The apparatus uses pneumatics to regulate the applied loads and uses the concept of an unbalanced load to simulate ballooning of different portions of the roof cover during cyclic winds.

Another known apparatus for evaluating the fatigue of fasteners includes a horizontal platen to which the roof deck, insulation and fastened membrane are attached. The membrane has loose ends attached to arms of the apparatus, which move horizontally. The platen moves vertically at a frequency eight times that of the arm. These different frequencies allow a wave-like action which closely simulates the ripple effect of the membrane. However, because the geometry of the platen and arms is not adjustable, the same motion is applied to all types of membranes. Furthermore, it is not known if a given force during the cycle of the apparatus is applied at the angle at which forces would be exerted under actual conditions. Moreover, the actual forces imparted to the sample in the apparatus are not known.

A drawback for both fastener fatigue apparatuses described above is the fact that only one fastener is used in the test, a relatively narrow strip of membrane is fastened, and the contribution and effect of adjacent fasteners is not considered.

SUMMARY OF THE INVENTION

By the apparatus according to the present invention, the fatigue characteristics of roof covers can be evaluated. A row of three fasteners spaced at a spacing commonly used in actual roof cover installations can be tested. The apparatus has sufficient load and strain capability to test reinforced and unreinforced roof membranes. The angle of application of forces to the test membrane is sufficiently adjustable to evaluate reinforced and non-reinforced roof systems including roof covers and fasteners. Test results are repeatable in that the same forces can be applied to a roof cover sample for the same number of cycles as in previous tests.

All of the forces imparted to the test samples in the present invention are imparted through a fluid pressure system, in particular, a pneumatic system. The pneumatic system allows easy adjustment of the force applied to the test sample by varying the pressure of the compressed air and/or the number of pneumatic cylinders employed. In addition, the apparatus has the capability for quick cycling through the use of electromechanical solenoid valves in connection with a pneumatic system. Adequate strain capability is provided by the use of pneumatic cylinders having sufficient stroke capacity.

In order to achieve these and other objects according to the present invention, the apparatus includes opposed sets of pneumatic cylinders through which forces are applied to the test membrane. The forces, or load, can be applied by any number of the pistons, depending on the total loading required. A center platen is provided in the apparatus for anchoring a test sample, and the pistons of the pneumatic cylinders are connected to edges of the sample. The cylinders are adjustable horizontally, and the center platen is adjustable vertically to allow for any angle of force application from nearly 0° to greater than 45°. The pistons work in tension. In order to control the pressure of air to each group of pistons, the air pressure is regulated to a desired level and directed to one set of pistons by an electro-pneumatic solenoid valve. A pressure switch monitors the pressure rise in the group of cylinders being loaded, and when the pressure reaches a pre-set level, the pressure switch signals the solenoid valve to switch the flow of pressure fluid to the opposite group of cylinders. The air in the cylinders from which the compressed air is switched is not exhausted directly to atmosphere. Instead, the air is exhausted through a pressure regulating valve which is adjusted to maintain a lower pre-set pressure, which is the lower load on the cylinders. The switching continues automatically for the required number of cycles.

DETAILED DESCRIPTION OF THE PREFERRED EMBODIMENT

Figure 1:
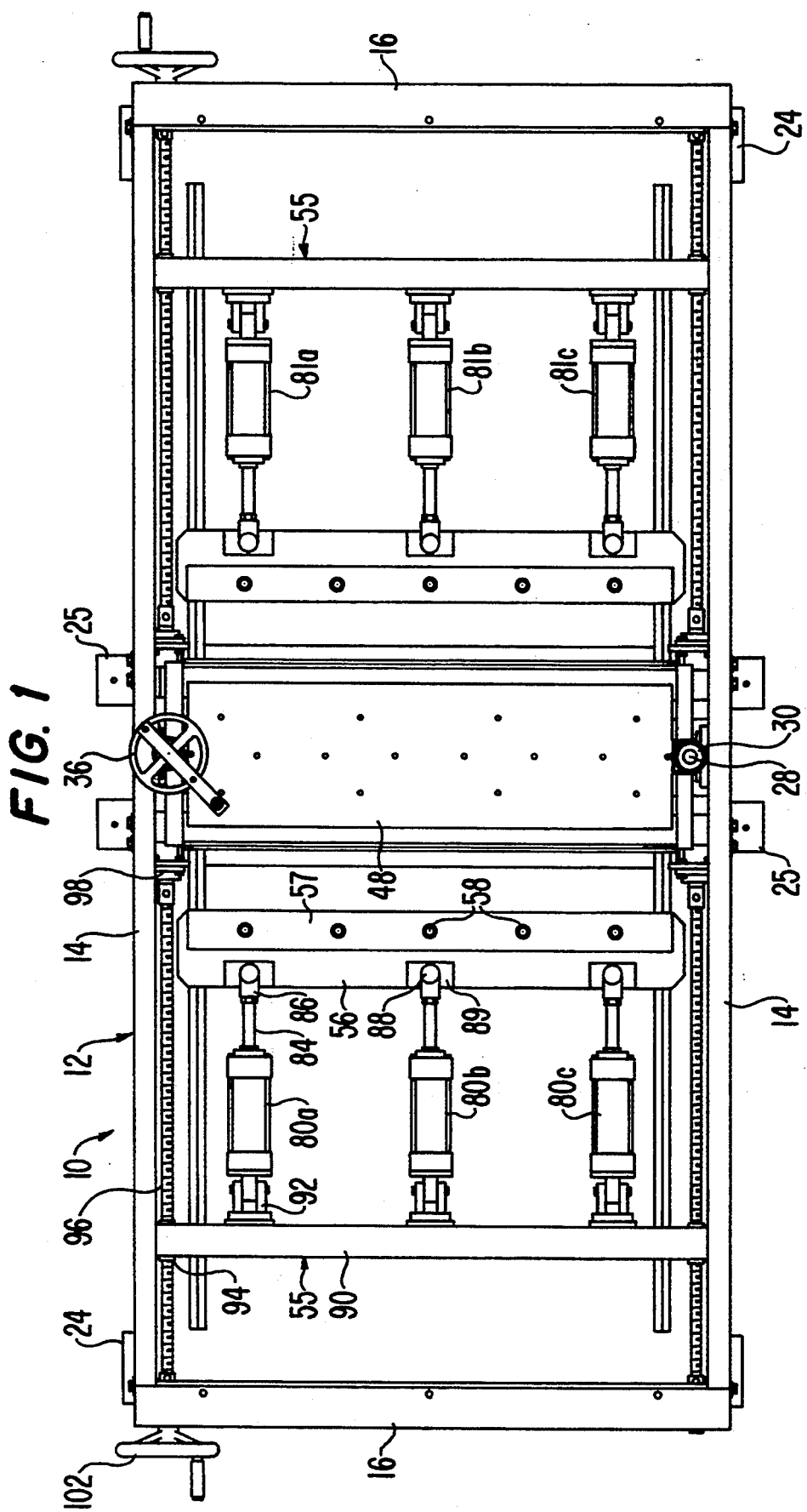
FIG. 1 is a top plan view of a roof cover fatigue tester according to the present invention.
Figure 2:
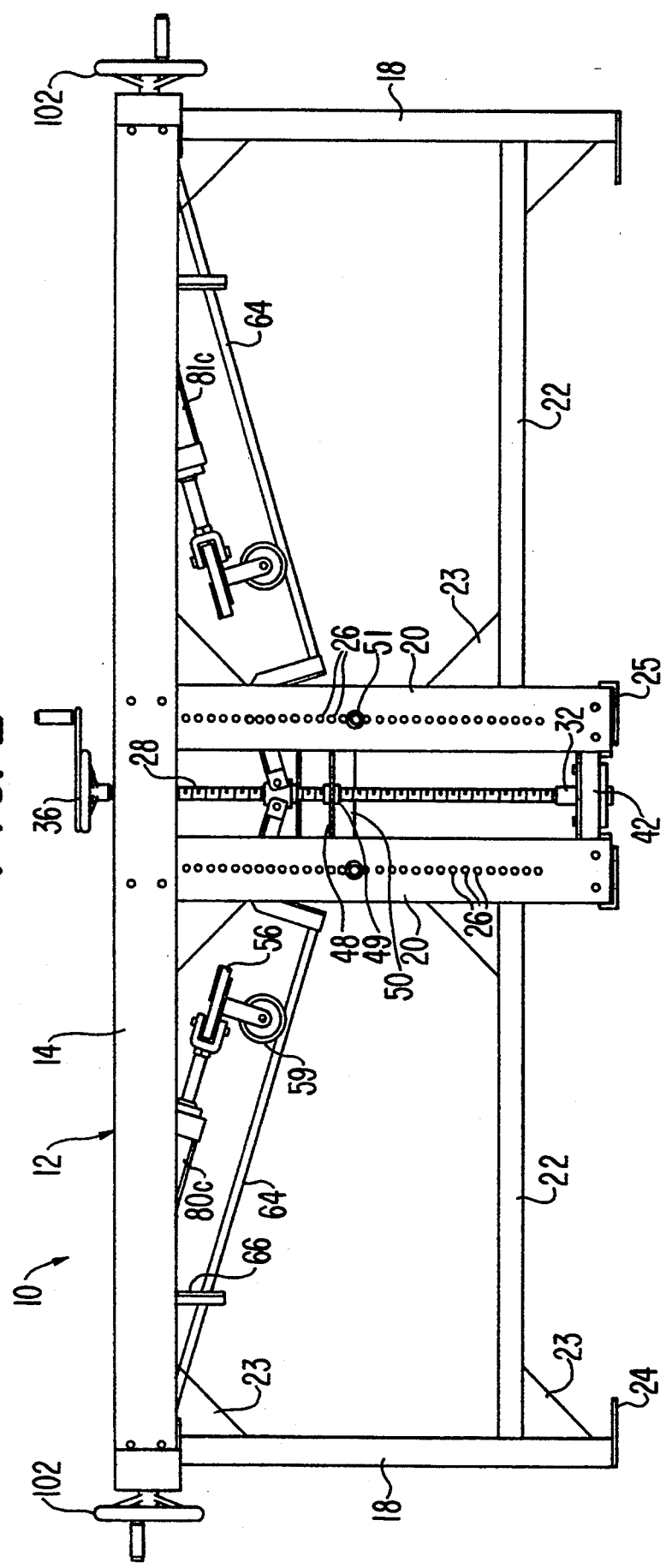
FIG. 2 is a side view of the fatigue tester of FIG. 1.
Figure 3:
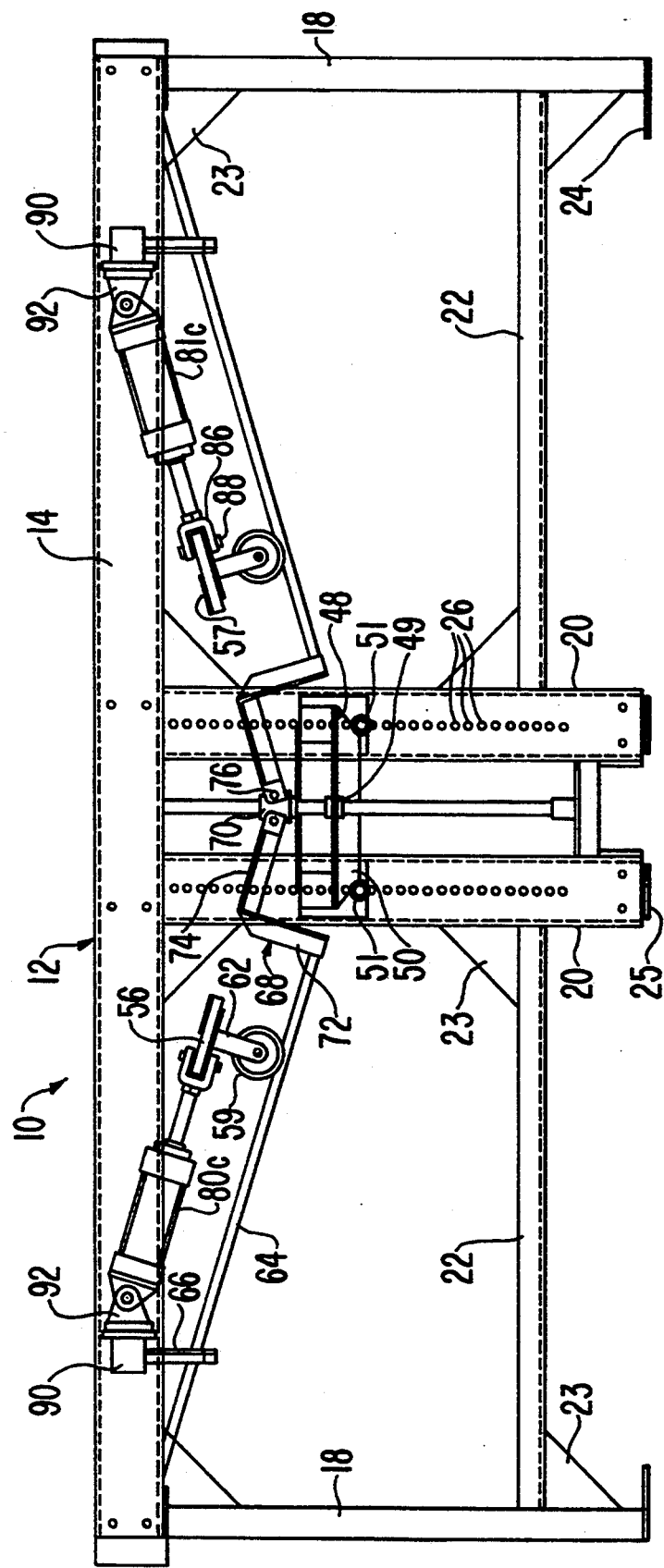
FIG. 3 is a side view of the fatigue tester of FIG. 1, showing parts hidden in FIG. 2.
Figure 4:
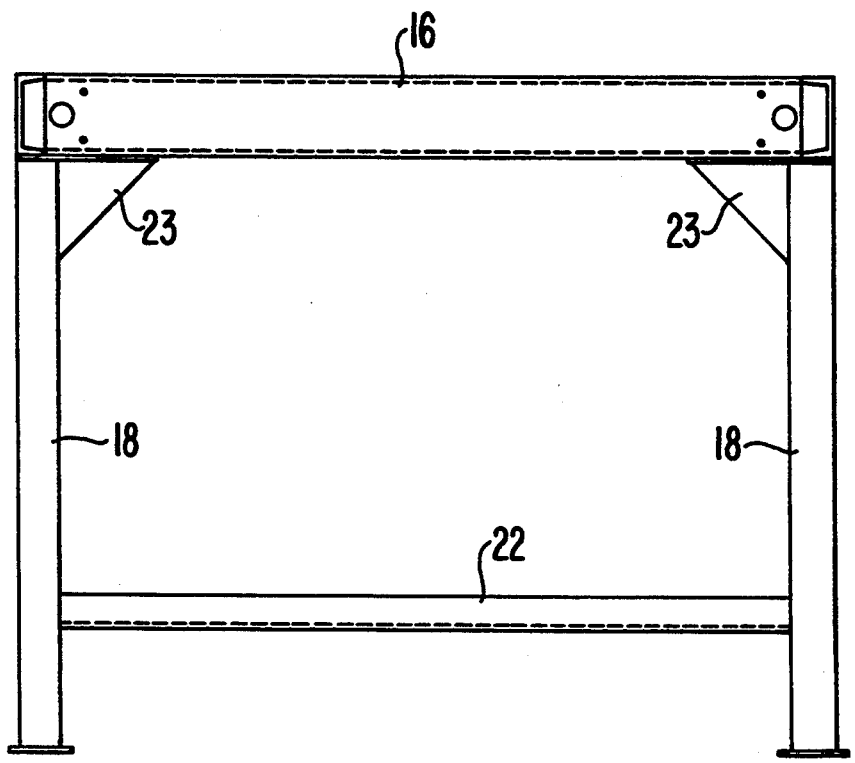
FIG. 4 is an end view of the fatigue tester of FIG. 1.

As can be seen from FIGS. 1-4, the single-ply roof cover fatigue tester according to the present invention, which is designated generally by the reference numeral 10, defines a support structure of generally rectangular parallelepiped shape made of steel members which is designed to rest on a floor and extend upward to approximately table height. At the top of the tester 10 is a rectangular frame 12 made of side frame members 14 and end frame members 16, such as channel members, secured together, such as by bolting, so that the channels defined by the frame members 14, 16 face inwardly toward one another. The frame 12 is supported by legs 18 positioned at the corners of the frame and near the centers of each of the side frame members. Two intermediate legs 20 are secured to each of the side frame members 14 on opposite sides of a transverse vertical central plane extending through the side members. Horizontal brace members 22 extend between adjacent leg members 18 and 20, except that brace members do not extend between adjacent intermediate legs 20. However, connecting members extend between each intermediate leg 20 on one side of the fatigue tester 10 and its facing intermediate leg 20 on the opposite side of the fatigue tester, these connecting members being connected at the bottoms of the intermediate legs 20. Gussets 23 are also used for strength and rigidity. The intermediate legs 20 are channel members whose channels face the intermediate leg 20 on the opposite side of the fatigue tester 10. Apertured horizontal foot plates 24, 25 are secured at the bottoms of the legs 18 and the intermediate legs 20, respectively, so that the tester 10 can be anchored to a floor by, for example, bolts. A series of closely spaced apertures 26 is arranged vertically on each intermediate leg 20, the apertures 26 extending through the bottom of the channel.

A vertical threaded rod 28 is mounted for rotation midway between the intermediate legs 20 on each side of the fatigue tester 10 and spaced slightly from its side and toward the center of the frame 12. Each vertical threaded rod 28 is journalled at its upper end in a pillow block bearing 30 secured to the side frame member 14, and its lower end is journalled in a bushing 32. A hand wheel 36 is secured at the top of one of the vertical threaded rods 28 to permit manual rotation of the rod. The vertical threaded rod 28 on one side of the fatigue tester 10 is mechanically connected to the lower end of the threaded rod 28 on the opposite of the tester so that the rods rotate together. The mechanical connection can be accomplished by any of various known transmission arrangements, such as by chain sprockets secured at the bottom end of each of the threaded rods 28 and a sprocket chain extending around and engaging the sprockets, so that rotation of the hand wheel 36 not only causes rotation of the threaded rod 28 on which the hand wheel is mounted, but also corresponding rotation of the threaded rod on the opposite side of the fatigue tester 10. A cover 42 extends over the top and along the sides of the mechanical transmission arrangement and is secured at its ends to the intermediate legs 20. The bushing 32 extends through the cover 42 adjacent to each end thereof.

A movable structure for receiving a roof cover sample and associated fasteners, such as a platen 48, extends transversely across the fatigue tester 10, from the intermediate legs 20 on one side of the fatigue tester to the intermediate legs on the opposite side. A threaded sleeve 49 is fixed at each end of the platen 48, and the vertical threaded rods 28 are received in the threaded sleeves 49 in threaded engagement with the threaded sleeves. When the hand wheel 36 is rotated, both vertical threaded rods 28 rotate, and the platen 48 moves either up or down on the threaded rods. Each end of the platen 48 has a portion 50 which is adjacent to and in alignment with the apertures 26 in the intermediate legs 20. Pins, bolts or the like 51 are inserted in selected apertures 26 to engage the portions 50 of the platen and, thereby, prevent the platen 48 from moving from its set position during the operation of the fatigue tester 10.

Figure 5:
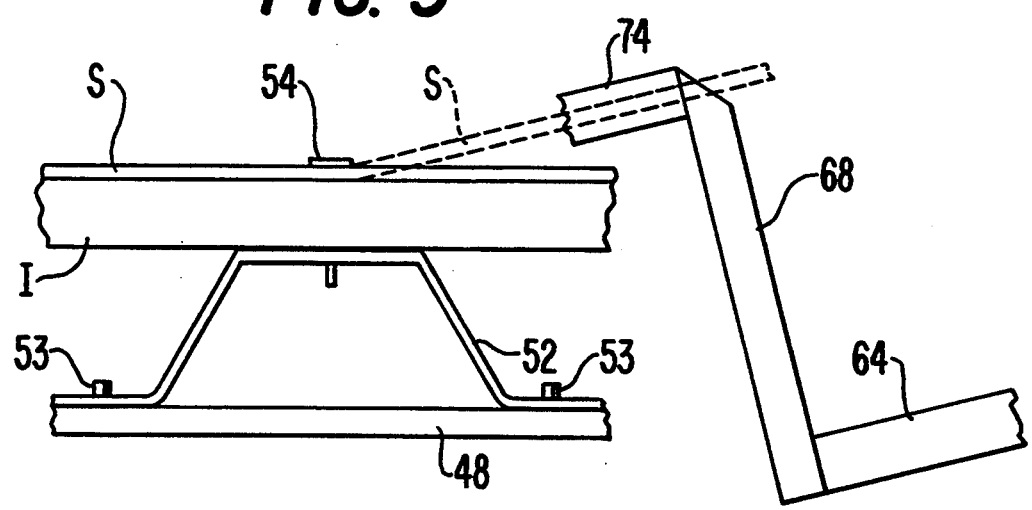
FIG. 5 is a schematic end view of a platen of the fatigue tester of FIG. 1, with a roof cover sample in place.

As can be seen from FIG. 5, a roof deck structure 52, for example, of the type actually to be used with the roof cover, is mounted on the platen 48 by bolts 53. A roof-cover sample S, a single-ply membrane, to be tested for fatigue is attached to the roof deck 52 by fasteners 54, with a layer of insulation I interposed. The platen is long enough that at least three of the fasteners 54 can be arranged in a straight line at a spacing commonly used in actual roof cover installations, for example, on the order of 6 to 18 inches on center. The portion of the roof-cover sample S fastened by the fasteners 54 defines a reference plane relative to which the angle of the application of the tension force is determined.

A subassembly 55 for exerting a tension force on a roof-cover sample mounted on the platen 48 is positioned on each side of the platen. The subassembly 55 includes an elongate anchoring member 56 extending across the frame 12, parallel to the length of the platen 48. An elongate clamping plate 57 extends along the top of the anchoring member 56 and is secured to the anchoring member 56 by a plurality of spaced, releasable fasteners 58, such as bolts. A strip portion of the clamping plate 57 projects toward the platen 48 from the fasteners 58. The fasteners 58 can be loosened so that the clamping plate 57 can be raised relative to the anchoring member 56 sufficiently to allow a side edge of the roof-cover sample to be received between the clamping plate 57 and the anchoring member 56. Tightening of the fasteners 58 clamps the clamping plate 57 against the anchoring member 56 and retains the edge of the roof-cover sample S between the clamping portion of the clamping plate 57 and the anchoring member 56. A caster 59 having a V-shaped annular groove 60 in its circumference is supported for rotation at each end of the elongate anchoring member 56, on the underside of the anchoring member. The caster 59 is journalled in a bracket 62. The caster 59 is supported by a rail 64 defining a V-shaped upper surface which is received in the V-shaped groove 60 of the caster. The rail 64 extends parallel to the sides of the fatigue tester 10 and perpendicular to the length of the anchoring member 56. An end of the rail 64 distal to the platen 48 is supported by a bracket 66 which defines an opening through which the rail 64 extends, the rail resting on the bottom of the bracket. An end of the rail 64 adjacent to the platen 48 is connected by an angle element 68 connected to a threaded sleeve 70 through which the vertical threaded rod 28 extends in threaded engagement. The angle element 68 has a first leg 72 which extends generally upward from the end of the rail 64 and a second leg 74 which extends at substantially a right angle to the first leg to a pivot connection 76 on the threaded sleeve 70. Thus, when the hand wheel 36 is rotated, not only does the platen 48 move up and down, but the threaded sleeve 70 and, thus, the adjacent end of the caster rail 64 move up and down as well. The height of the bracket 66 supporting the distal end of the caster rail 64 is fixed. Therefore, operation of the hand wheel 36 changes the inclination of the caster rail 64. After adjustment of the height of the platen 48, the height is fixed by the pins, bolts or the like 51 extending through the pertinent openings 26 in the intermediate legs 20.

Figure 7:
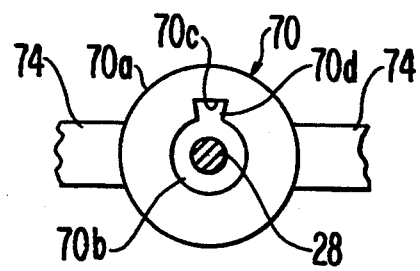
FIG. 7 is a bottom view of a threaded sleeve on a vertical threaded rod.

As can be seen from FIG. 7, which is a bottom view of the threaded sleeve 70, the threaded sleeve 70 is made in two pieces, a housing 70a having a central opening which is not threaded and a core member 70b having a central opening which is threaded. The threads of the central opening of the core member 70b engage the threads of the vertical threaded rod 28. The housing 70a includes a slot or keyway 70c which receives a tab 70d on the core member 70b. As a result, when the vertical threaded rod 28 rotates, the housing 70a prevents the core member 70b from rotating with the vertical threaded rod. Instead, the threaded sleeve 70 moves as a unit up or down along the vertical threaded rod 28. However, the housing 70a can be lifted off of the core member 70b to allow the core member 70b to be rotated while the vertical threaded rod 28 is stationary. This allows the core member 70b to be adjustable relative to the platen 48. In order to simulate real wind uplift conditions, the line along which the roof-cover sample S is pulled should pass through the area of engagement of the fasteners 54 with the roof-cover sample S. As can be appreciated from FIG. 5, the roof-cover sample S will be pulled along a line which is parallel to the rails 64. However, various thicknesses of insulation I may be used in a test and, therefore, the distance between the threaded sleeve 70 and the platen 48 must be adjustable to allow the line along which the roof-cover sample S is pulled to pass through the area of engagement of the fasteners 54 with the roof-cover sample for various thicknesses of insulation I. The structure of the threaded sleeve 70 described above enables such adjustment.

A plurality of pressure fluid cylinders, such as pneumatic cylinders 80a–80c and 81a–81c, is connected to each of the elongate anchoring members 52. A piston of each pneumatic cylinder 80a–80c, 81a–81c is connected through a piston rod 84 and a clevis 86 to the anchoring member 56. A pin 88 extends through an opening in the anchoring member 56 and aligned openings in the clevis 86 to secure the piston 82 to the anchoring member. Plates 89 are interposed between the anchoring members 56 and the clevises 86 to provide the proper fit between the anchoring members and the clevises. The pneumatic cylinders 80a–80c, 81a–81c are connected to a movable support element 90 through another conventional clevis and pin arrangement 92. The pistons each have a stroke, for example, 5 inches, sufficient to fully strain the test sample S.

The movable support element 90 extends parallel to the anchoring member 56, from one side of the frame 12 to the other. A threaded sleeve 94 having a horizontal axis is fixed in each end of the movable support element 90 and is received on a horizontal threaded rod 96 or 97 mounted for rotation just inside the side of the frame 12. An end of the each horizontal threaded rod 96, 97 adjacent to the platen 48 is journaled for rotation in a bearing 98 secured to the side of the frame 12 near the intermediate leg 20. A distal end of the horizontal threaded rod 96 extends through a bearing (not shown) mounted in the frame end member 16. A hand wheel 102 is mounted on the end of the horizontal threaded rod 96 outside the frame 12. Two horizontal threaded rods 96, 97 are arranged on each side of the platen 48. The horizontal threaded rods 96 at each end of the frame 12 are connected so that the motion of the horizontal threaded rod 97 having the hand wheel 102 is transmitted to the horizontal threaded rod 96 which does not have the hand wheel. Various conventional transmission mechanisms, such as sprockets mounted at the ends of the threaded rods and a sprocket chain connecting the sprockets, can be used. The transmission mechanism can be located just inside the frame end members 16. The brackets 66 which support the rails 64 are mounted on the undersides of the movable support elements 90.

In operation, the height of the platen 48 is adjusted using the hand wheel 36 to achieve the angle of application of force desired. The roof cover test sample S is secured, usually through an insulation material, to the roof deck 52 on the platen 48 using the fasteners 54 to be tested with the roof cover test sample. The edges of the sample are secured between the anchoring member 56 and the clamping plate 57, and the fasteners 54 on the anchoring member are passed through the sample and tightened to clamp the sample. Using the hand wheels 102 at the ends of the apparatus, the horizontal threaded rods 96, 97 are turned to move the support elements 90 toward or away from the edges of the sample so that the fluid pressure cylinders 80a–80c, 81a–81c are in the desired starting position, in which the sample is held taut.

Figure 6:
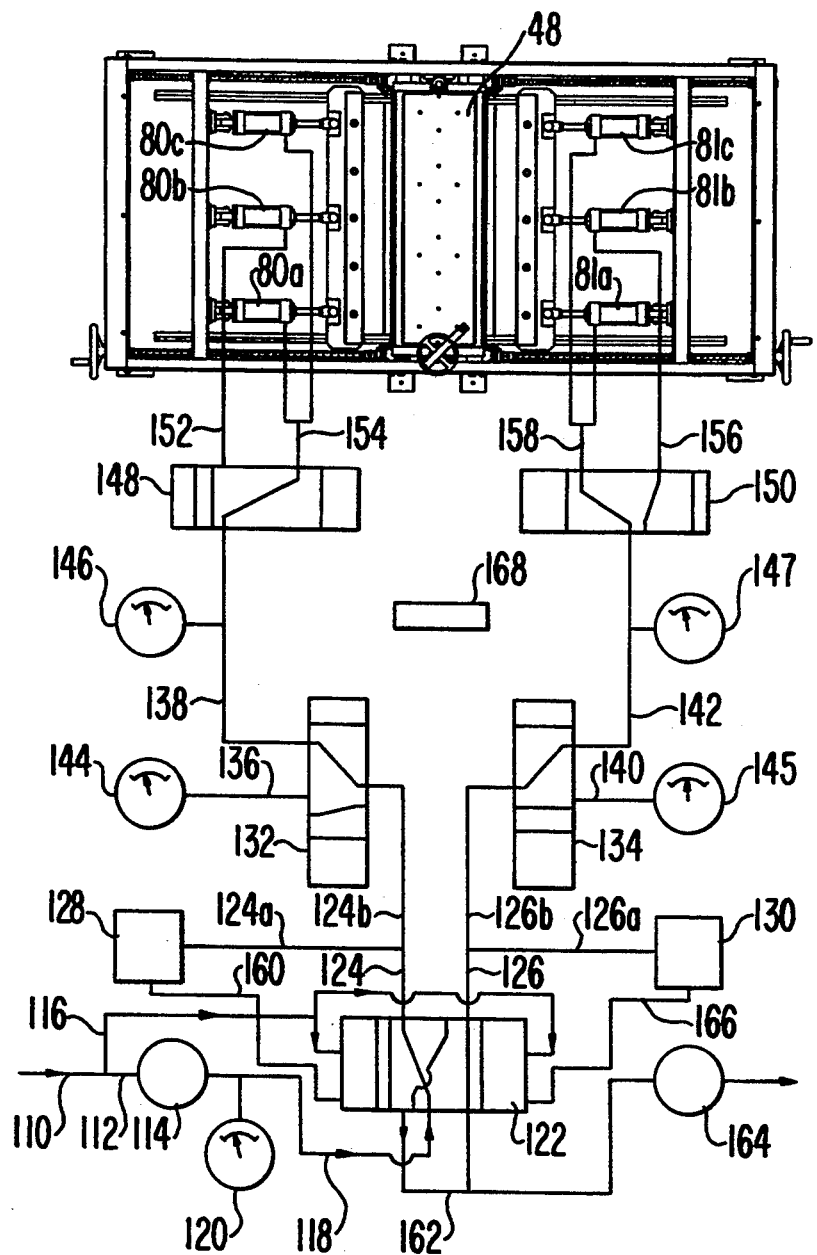
FIG. 6 is a schematic illustration of the control system for the fluid pressure cylinders of the fatigue tester according to the present invention.

As can been seen from FIG. 6, which schematically shows a control system for the fatigue tester 10, a source of fluid pressure, such as a compressor, is connected to the control system by an inlet line 110. The inlet line 110 has one branch line 112 which passes through an adjustable pressure regulator 114 and another branch line 116 which is unregulated. Pressure fluid exits the adjustable pressure regulator 114 through an outlet line 118 at a desired, preset pressure lower than the pressure of the fluid from the source of pressure fluid. The pressure of the fluid in the outlet line 118 is indicated by a pressure gauge 120. The outlet line 118 from the adjustable pressure regulator 114 extends to an inlet port of an electro-pneumatic solenoid valve 122. Depending on the position of the solenoid valve 122, the pressure fluid entering the solenoid valve flows either through an outlet line 124 or an outlet line 126. The branch line 116 carrying the unregulated pressure fluid is connected to ports of the solenoid valve 122 to change the position of the valve element. Each of the outlet lines 124, 126 from the solenoid valve 122 has a first branch 124a, 126a, respectively, connected to a pressure switch 128, 130 and a second branch 124b, 126b connected to a mode selection valve 132, 134, which can be manually operable. Pressure fluid in the lines 124b and 126b flows through the mode selection valves 132 and 134 to one of two outlet lines, depending on the position of the mode selection valve. The mode selection valve 132 is connected to outlet lines 136 and 138, and the mode selection valve 134 is connected to outlet lines 140 and 142. Each outlet line 136 and 140 is connected only to a respective pressure gauge 144, 145. Each outlet line 138 and 142 is connected to a respective pressure gauge 146, 147 and to a respective cylinder selection valve 148, 150, which can be manually operable. Pressure fluid entering the cylinder selection valves 148, 150 from the lines 138, 142 flows out through one of two outlet lines, depending on the position of the cylinder selection valve. Outlet lines 152 and 154 are connected to the cylinder selection valve 148, and outlet lines 156 and 158 are connected to the cylinder selection valve 150. The electro-pneumatic solenoid valve 122, the mode selection valves 132, 134, and the cylinder selection valves 148, 150 are all conventional.

The outlet line 152 is connected to the center cylinder 80b on one side of the platen 48, and the outlet line 156 is connected to the center cylinder 81b on the opposite side of the platen 48 from the cylinder 80b. The outlet line 154 is connected to the cylinders 80a and 80c, and the outlet line 158 is connected to the cylinders 81a and 81c. The cylinder selection valves 148, 150 can be set by hand to cause fluid to flow to either the single center cylinders 80b and 81b or the two other cylinders 80a, 80c and 81a, 81c, respectively, depending upon the amount of force needed for the roof cover sample being tested. The fluid pressure lines in the control system can be hoses, and it is contemplated that other groupings of the cylinders 80a–80c and 81a–81c can be selected by changing the arrangements of the hoses which comprise the outlet lines 152, 154, 156, 158 of the cylinder selection valves 148, 150. For example, the outlet lines 152 and 156 can comprise hoses connected to all three of the cylinders on their respective sides of the platen 48. As a result, in one position of the cylinder selection valves 148, 150, pressure fluid will flow to all three of the cylinders. As another variation, the cylinder selection valves 148, 150, which are two-way valves, can be replaced by three-way cylinder selected valves which can cause fluid pressure to flow through any one of three outlets, each outlet being connected to different cylinders or groupings of cylinders.

In order to calibrate the tester 10 prior to use, the mode selection valves 132 and 134 are manually set to a calibration mode, in which fluid flows out of the mode selection valves through outlet lines 136 and 140. The source of pressure fluid is actuated, thereby causing the pressure fluid to flow through the adjustable pressure regulator 114, through the electro-pneumatic solenoid valve 122, and alternately through the outlet lines 124 and 126. In the calibration mode, pressure fluid entering the mode selection valves 132, 134 flows through the outlet lines 136, 140 to only the pressure gauges 144, 145. The pressure fluid leaving the electro-pneumatic solenoid valve 122 through one of the outlet lines, for example, the outlet line 124, flows to the pressure switch 128 and through the mode selection valve 132 to the gauge 144. The gauge 144 indicates the increase in pressure in the system up to the point for which the pressure switch 128 is set. At that point, the pressure switch 128 sends an electrical signal through an electrical line 160 to a solenoid in the electro-pneumatic solenoid valve 122, causing the valve to change position. The change in position causes the pressure fluid to flow out of the electro-pneumatic solenoid valve 122 through the outline line 126 rather than through the outlet line 124 and simultaneously connects the outlet line 124 with an exhaust line 162, which is connected through a pressure regulating valve 164 to the atmosphere. By adjusting the pressure switch 128, the pressure at which the pressure switch 128 sends a signal to the electro-pneumatic solenoid valve 122 is changed, and that pressure can be determined by reference to the gauge 144.

The pressure regulating valve 164 is adjustable. Adjusting the pressure regulating valve 164 adjusts the minimum pressure which is maintained in the portion of the system from which pressure is being relieved. Similarly, the pressure switch 130, can be adjusted. The pressure switch 130 sends an electrical signal to a solenoid in the electro-pneumatic solenoid valve 122 through an electrical line 166.

When calibration is complete, the mode selection valves 132, 134 are switched to an operation mode position in which pressure fluid flows from the inlet lines 124b, 126b to the outlet lines 138, 142, which are connected to respective pressure gauges 146, 147 and cylinder selection valves 148, 150. The pressure fluid flows through the pressure regulator 114 to reduce the pressure to the desired level, through the line 118 to the electro-pneumatic solenoid valve 122 and through one of the outlet lines, for example, the outlet line 124. Pressure fluid in the outlet line 124 flows to the pressure switch 128, through the mode selection valve 132 to the pressure gauge 146 and to the cylinder selection valve 148, and from the cylinder selection valve 148 either through the outline line 152 to the cylinder 80b or through the outlet line 154 to the cylinders 80a, 80c. The pressure in the pressure fluid cylinder 80b or cylinders 80a, 80c increases, and the pressure in the pressure switch 128 increases correspondingly until the desired maximum pressure is reached. At the set maximum pressure, the pressure switch 128 sends an electrical signal to the electro-pneumatic solenoid valve 122, which changes the position of the valve. The change in position causes the fluid pressure in the cylinder 80b or cylinders 80a, 80c to exhaust through the cylinder selection valve 148, the mode selection valve 132, the electro-pneumatic solenoid valve 122, the outlet line 162 and the pressure regulating valve 164 to the atmosphere. At the same time, the switching of the electro-pneumatic solenoid valve 122 connects the source of fluid pressure in the inlet line 118 to the outlet line 126, thereby causing the pressure fluid to flow to the pressure switch 130 and through the mode selection valve 134 to the pressure gauge 145 and the cylinder selection valve 150. From the cylinder selection valve 150, the pressure fluid flows to either the pressure fluid cylinder 81b or the pressure fluid cylinders 81a and 81c, depending upon the position of the valve. When the pressure in the selected pressure fluid cylinder or cylinders reaches its preset maximum, the pressure in the pressure switch 130 simultaneously reaches the same maximum pressure, at which point the pressure switch 130 sends an electrical signal to the electro-pneumatic solenoid valve 122 to switch the valve to its other position. The back-and-forth switching of the electro-pneumatic valve 122 continues until the desired number of cycles has been reached. A counter 168 having a visible read-out is provided in the control system. It can be a conventional electrical counter connected to either one of the pressure switches 128, 130. By such a connection, the pressure switch 128 or 130 indexes the counter by one each time the pressure switch sends an electrical signal to the electro-pneumatic solenoid valve 122, which is each time the pressure in the cylinder or cylinders on one side of the platen 48 reaches a maximum.

By the action of the control system, the fluid pressure in the cylinder or cylinders on one side of the platen 48 is increased, thereby increasing the tension force along one edge of the roof cover sample on the platen 48. Upon the switching of the electro-pneumatic solenoid valve 122, the pressure in the cylinder or cylinders on the opposite side of the plate 48 increases, thereby increasing the tension force on the adjacent edge of the roof cover sample S. Simultaneously, the tension force on the first edge of the roof cover sample S is reduced, but not entirely relieved. As the electro-pneumatic solenoid valve 122 is switched back and forth, the higher tension force is applied alternately to opposite sides of the roof cover-sample S for the desired number of cycles.

It will be apparent to those skilled in the art and it is contemplated that variations and/or changes in the embodiments illustrated and described herein may be made without departure from the present invention. For example, the pressure switches 128 and 130 can be replaced by pressure transducers, and the pressure regulating valve 164 can be replaced by a solenoid valve. The pressure transducers can each have upper and lower pressure limits and can transmit signals when either limit is reached. In response to reaching a pressure limit, an electrical signal is sent to a computer which is connected to the solenoid valve to control the operation of the valve. In such an embodiment, when either of the transducers reaches the upper pressure limit, a signal is sent to the computer, which in turn sends a signal to the electro-pneumatic solenoid valve 122 to switch the valve 122 from one position to the other. At the same time, the computer sends a signal to the solenoid valve replacing the pressure regulating valve 164 to open the solenoid valve to allow pressure to be relieved from the pneumatic cylinders in which the maximum pressure has just been reached. The pressure is relieved until it reaches a minimum level equal to the minimum point set on the pressure transducer. At that point, the transducer sends a signal to the computer, which in turn sends a signal to the solenoid valve to close the valve and, thereby, prevent pressure in the pneumatic cylinders going below the minimum set pressure. Accordingly, it is intended that the foregoing description is illustrative only, not limiting, and that the true spirit and scope of the present invention will be determined by the appended claims.

We claim:

1. Apparatus for testing the fatigue of single-ply roof covers, comprising:
   a support structure;
   a movable structure for receiving a roof cover test sample and associated fasteners, said movable structure being mounted for movement relative to said support structure;
   means for applying a tension force to the roof cover test sample on opposite sides of the fasteners; and
   means for alternately increasing first the tension force applied to the roof cover test sample on one side of the fasteners and then on the opposite side of the fasteners while maintaining a minimum tension force on the side whose tension force is not being increased.

2. The apparatus of claim 1, wherein the roof cover sample has a portion fastened to said movable structure, the fastened portion defines a plane, and the tension force is applied at an angle relative to said plane, the apparatus further comprising means for adjusting the angle of the application of the tension force.

3. The apparatus of claim 1, wherein said means for alternately increasing comprises means for increasing the tension force to a maximum force, the apparatus further comprising means for adjusting said maximum force.

4. The apparatus of claim 1, further comprising means for adjusting said minimum tension force.

5. The apparatus of claim 1, further comprising means for indicating the tension force being applied to the roof cover test sample.

6. The apparatus of claim 1, wherein said movable structure has a length sufficient to support a roof cover sample and a plurality of fasteners arranged in a straight line and spaced at a spacing commonly used in actual roof cover installations.

7. The apparatus of claim 6, wherein said spacing is on the order of 6 to 18 inches on center.

8. The apparatus of claim 6, wherein said plurality of fasteners comprises at least three fasteners.

9. The apparatus of claim 6, wherein said fasteners intersect said roof cover sample, and said means for applying a tension force comprises means for applying a tension force along a line passing through the intersection of said fasteners and said roof cover sample, the apparatus further comprising means for adjusting the line along which the tension force is applied in order to accommodate roof cover samples of different thicknesses.

10. The apparatus of claim 1, further comprising means for indicating the number of times the increasing tension force alternates.

11. The apparatus of claim 1, further comprising means for calibrating said means for applying a tension force.

12. The apparatus of claim 1, wherein said means for applying a tension force comprises means for fully straining the test sample.

13. Apparatus for testing the fatigue of single-ply roof covers, comprising:
   a support structure;
   a movable structure for receiving a roof cover test sample and associated fasteners, said movable structure being mounted for movement relative to said support structure, the roof cover sample having a portion fastened to said movable structure, the fastened portion defining a plane;
   means for applying a tension force to the roof cover test sample on opposite sides of the fasteners at an angle relative to said plane;
   means for alternately increasing first the tension force applied to the roof cover test sample on one side of the fasteners, and then on the opposite sides of the fasteners; and
   means for adjusting the angle of application of the tension force.

14. Apparatus for testing the fatigue of single-ply roof covers, comprising:
   a support structure;
   a movable structure for receiving a roof cover test sample and associated fasteners, said movable structure being mounted for movement relative to said support structure;
   means for applying a tension force to the roof cover test sample on opposite sides of the fasteners;
   means for alternately increasing first the tension force applied to the roof cover test sample on one side of the fasteners and then on the opposite side of the fasteners to a maximum tension force; and
   means for adjusting said maximum force.

* * * * *